United States Patent [19]

Borzatta et al.

[11] Patent Number: 5,198,546
[45] Date of Patent: Mar. 30, 1993

[54] PIPERIDINE-TRIAZINE COMPOUNDS FOR USE AS STABILIZERS FOR ORGANIC MATERIALS

[75] Inventors: Valerio Borzatta, Bologna; Giuseppe Cantatore, Bari, both of Italy

[73] Assignee: Ciba-Geigy Corporation, Ardsley, N.Y.

[21] Appl. No.: 608,408

[22] Filed: Nov. 2, 1990

[30] Foreign Application Priority Data

Nov. 10, 1989 [IT] Italy .................. 22341 A/89

[51] Int. Cl.$^5$ .................................... C07D 403/00
[52] U.S. Cl. .................................... 544/198; 544/209; 544/212
[58] Field of Search .................. 544/198, 209, 212

[56] References Cited

U.S. PATENT DOCUMENTS

| | | | |
|---|---|---|---|
| 4,086,204 | 4/1978 | Cassandrini et al. | 524/100 |
| 4,108,829 | 8/1978 | Cassandrini et al. | 544/198 |
| 4,186,507 | 3/1980 | Cantatore | 524/100 |
| 4,234,728 | 11/1980 | Rody et al. | 544/198 |
| 4,315,859 | 2/1982 | Nikles | 524/100 |
| 4,331,586 | 5/1982 | Hardy | 524/100 |
| 4,335,242 | 6/1982 | Wiezer et al. | 524/100 |
| 4,426,472 | 1/1984 | Berner | 524/100 |
| 4,477,615 | 10/1984 | Raspanti et al. | 524/100 |
| 4,504,610 | 3/1985 | Fontanelli et al. | 524/100 |
| 4,530,950 | 7/1985 | Raspanti et al. | 524/100 |
| 4,547,548 | 10/1985 | Cantatore | 544/198 |
| 4,863,981 | 9/1989 | Gugumus | 524/100 |
| 4,883,870 | 11/1989 | Cantatore | 524/100 |
| 5,039,722 | 8/1991 | Cantatore | 544/198 |

FOREIGN PATENT DOCUMENTS

| | | |
|---|---|---|
| 0117229 | 8/1984 | European Pat. Off. |
| 53775 | 5/1986 | European Pat. Off. |
| 72009 | 9/1988 | European Pat. Off. |
| 292437 | 11/1988 | European Pat. Off. |
| 350444 | 1/1990 | European Pat. Off. |
| 354184 | 2/1990 | European Pat. Off. |
| 63-196654 | 8/1988 | Japan. |

OTHER PUBLICATIONS

Derwent Abst. 90–019543/03.
Chem. Abst. 105, 209942q (1986).

Primary Examiner—Kriellion S. Morgan
Attorney, Agent, or Firm—Luther A. R. Hall

[57] ABSTRACT

The present invention relates to novel piperidine-triazine compounds of the general formula (I)

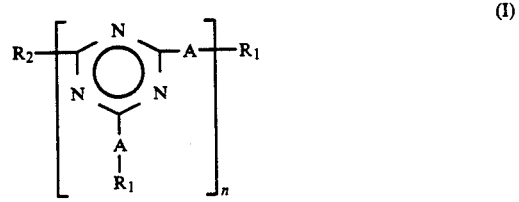

in which $R_1$ is e.g. methyl, acetyl or ($C_1$-$C_2$alkoxy)carbonyl, A is e.g. a group of the formula (IIa),

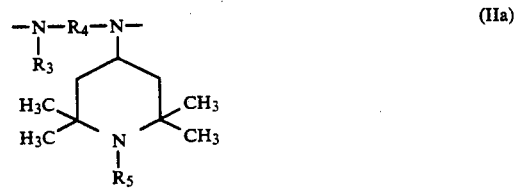

in which $R_3$ is e.g. hydrogen, methyl, 2,2,6,6-tetramethyl-4-piperidyl, 1,2,2,6,6-pentamethyl-4-piperidyl or 1-acetyl-2,2,6,6-tetramethyl-4-piperidyl, $R_4$ is e.g. $C_3$-$C_6$alkylene, $R_2$ is e.g. a group $R_1$-A- and n is e.g. a number from 1 to 5.

The said compounds are effective as light stabilizers, heat stabilizers and oxidation stabilizers for organic materials.

7 Claims, No Drawings

PIPERIDINE-TRIAZINE COMPOUNDS FOR USE AS STABILIZERS FOR ORGANIC MATERIALS

The present invention relates to novel piperidine-triazine compounds, to their use as light stabilizers, heat stabilizers and oxidation stabilizers for organic materials, in particular synthetic polymers, and to organic materials thus stabilized.

It is known that synthetic polymers are subject to photooxidative degradation when they are exposed to sunlight or other sources of ultraviolet light in the presence of oxygen.

For their use in practice, it is therefore necessary to add to them suitable light stabilizers, such as certain derivatives of benzophenone or benzotriazole, nickel complexes, substituted benzoic acid esters, alkylidenemalonates, cyanoacrylates, aromatic oxamides or sterically hindered amines.

Some triazine oligomers containing 2,2,6,6-tetramethyl-4-piperidyl groups and their use as stabilizers for synthetic polymers have been reported in U.S. Pat. Nos. 4,086,204, 4,315,859, 4,331,586, 4,335,242 and 4,477,615, European Patent 117,229 and Japanese Patent 63-196,654.

The present invention relates to novel piperidine-triazine compounds of the formula (I)

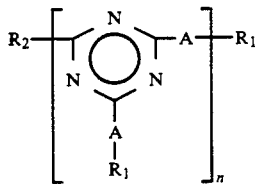

in which $R_1$ is $C_1$–$C_8$alkyl, $C_3$–$C_6$alkenyl, $C_7$–$C_9$phenylalkyl, $C_7$–$C_9$phenylalkyl mono-, di-or tri-substituted on the phenyl by $C_1$–$C_4$alkyl, $C_1$–$C_8$acyl or ($C_1$–$C_8$alkoxy)-carbonyl, A is a group of the formula (IIa) or (IIb)

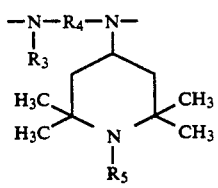

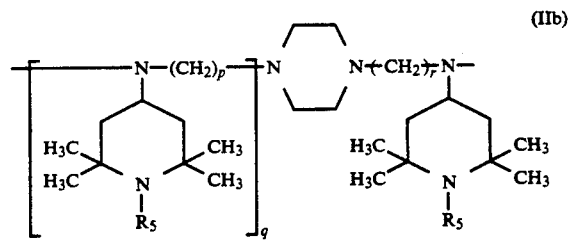

in which $R_3$ is hydrogen, $C_1$–$C_8$alkyl, $C_5$–$C_8$cycloalkyl which is unsubstituted or mono-, di- or tri-substituted by $C_1$–$C_4$alkyl, $C_7$–$C_9$phenylalkyl, $C_7$–$C_9$phenylalkyl mono-, di- or tri-substituted on the phenyl by $C_1$–$C_4$alkyl, or a group of the formula (III),

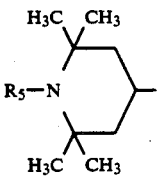

$R_5$ is hydrogen, $C_1$–$C_8$alkyl, O, OH, NO, $CH_2CN$, $C_1$–$C_{12}$alkoxy, $C_5$–$C_{12}$cycloalkoxy, $C_3$–$C_6$alkenyl, $C_7$–$C_9$phenylalkyl, $C_7$–$C_9$phenylalkyl mono-, di- or tri-substituted on the phenyl by $C_1$–$C_4$alkyl, or $C_1$–$C_8$acyl and $R_4$ is $C_2$–$C_{12}$alkylene, cyclohexylene, cyclohexylenedimethylene, methylenedicyclohexylene, xylylene or $C_4$–$C_{12}$alkylene interrupted by 1, 2 or 3 oxygen atoms or by a group >N—$CH_3$, p and r which can be identical or different are integers from 2 to 6 and q is zero or 1, and $R_2$ is OH, ONa, OK, $C_1$–$C_8$alkoxy, $C_3$–$C_6$alkenyloxy, $C_7$–$C_9$phenylalkoxy, $C_1$–$C_8$acyloxy or a group $R_1$-A-, with $R_1$ and A being as defined above, or $R_2$ can also be a group of the formula (IV)

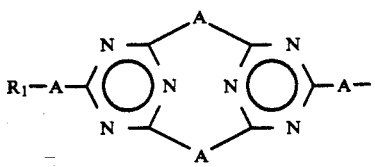

in which $R_1$ and A are as defined above and when $R_2$ is a group of the formula (IV), the terminal group $R_1$ which is outside of the brackets in the formula (I) is additionally a group

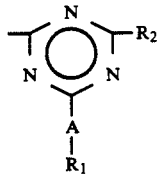

in which $R_1$ and A are as defined above and n is a number from 1 to 20.

Examples of $C_1$–$C_8$alkyl are methyl, ethyl, propyl, butyl, 2-butyl, isobutyl, pentyl, 2-pentyl, hexyl, heptyl, octyl and 2-ethylhexyl. $C_1$–$C_4$Alkyl, in particular methyl, is preferred.

Examples of alkoxy having not more than 12 carbon atoms are methoxy, ethoxy, propoxy, butoxy, isobutoxy, pentoxy, isopentoxy, hexoxy, heptoxy, octoxy, decyloxy and dodecyloxy, Heptoxy and octoxy are preferred.

Examples of ($C_1$–$C_8$alkoxy)carbonyl are methoxycarbonyl, ethoxycarbonyl, propoxycarbonyl, butoxycarbonyl, pentoxycarbonyl, hexoxycarbonyl and octoxycarbonyl.

Examples of $C_5$–$C_8$cycloalkyl which is unsubstituted or mono-, di- or tri-substituted by $C_1$–$C_4$alkyl are cyclopentyl, methylcyclopentyl, cyclohexyl, methylcyclohexyl, dimethylcyclohexyl, trimethylcyclohexyl, t-butylcyclohexyl, cycloheptyl and cyclooctyl. Cyclohexyl is preferred.

Representative examples of $C_5$–$C_{12}$cycloalkoxy $R_5$ are cyclopentoxy, cyclohexoxy, cycloheptoxy, cyclooctoxy, cyclodecyloxy and cyclododecyloxy. Cyclopentoxy and cyclohexoxy are preferred.

Examples of $C_3$-$C_6$alkenyl are allyl, 2-methylallyl, butenyl, pentenyl and hexenyl. Allyl is preferred.

Examples of $C_3$-$C_6$alkenyloxy are allyloxy, 2-methylallyloxy, butenyloxy, pentenyloxy and hexenyloxy.

$C_7$-$C_9$Phenylalkyl $R_1$, $R_3$ and $R_5$ can be unsubstituted or mono-, di- or tri-substituted on the phenyl by $C_1$-$C_4$alkyl and are preferably benzyl, methylbenzyl, dimethylbenzyl, t-butylbenzyl or 2-phenylethyl. Benzyl is particularly preferred.

An Example of $C_7$-$C_9$phenylalkoxy is benzyloxy.

Examples of $C_1$-$C_8$acyl are formyl, acetyl, propionyl, butyryl, isobutyryl, pentanoyl, hexanoyl, heptanoyl, octanoyl, benzoyl, acryloyl and crotonoyl. $C_1$-$C_8$Alkanoyl, $C_3$-$C_8$alkenoyl or benzoyl are preferred. Acetyl is particularly preferred.

Examples of $C_1$-$C_8$acyloxy are formyloxy, acetyloxy, propionyloxy, butyryloxy, isobutyryloxy, pentanoyloxy, hexanoyloxy, heptanoyloxy, octanoyloxy, benzoyloxy, acryloyloxy and crotonoyloxy. $C_1$-$C_8$alkanoyloxy, $C_3$-$C_8$alkenoyloxy and benzoyloxy are preferred.

Representative examples of $C_2$-$C_{12}$alkylene $R_4$ are ethylene, propylene, trimethylene, tetramethylene, pentamethylene, 2,2-dimethyltrimethylene, hexamethylene, trimethylhexamethylene, decamethylene and dodecamethylene. $C_2$-$C_6$Alkylene is preferred.

Representative examples of $C_4$-$C_{12}$alkylene $R_4$ interrupted by 1, 2 or 3 oxygen atoms are 4-oxaheptane-1,7-diyl, 4,7-dioxadecane-1,10-diyl and 4,9-dioxadodecane-1,12-diyl and 3,6,9-trioxaundecane-1,11-diyl; 4,7-dioxadecane-1,10-diyl and 4,9-dioxadodecane-1,12-diyl are preferred.

Representative examples of $C_4$-$C_{12}$alkylene $R_4$ interrupted by a group >N—$CH_3$ are the

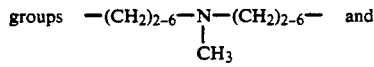

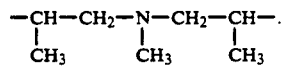

$R_5$ is preferably hydrogen, $C_1$-$C_4$alkyl, OH, $C_6$-$C_8$alkoxy, $C_5$-$C_8$cycloalkoxy, allyl, benzyl or acetyl, in particular hydrogen, methyl or acetyl.

Those compounds of the formula (I) are preferred in which $R_1$ is $C_1$-$C_6$alkyl, allyl, benzyl, $C_1$-$C_6$acyl or ($C_1$-$C_6$alkoxy)-carbonyl, A is a group of the formula (IIa) or (IIb) in which $R_3$ is hydrogen, $C_1$-$C_6$alkyl, cyclohexyl which is unsubstituted or mono-, di- or tri-substituted by $C_1$-$C_4$alkyl, benzyl or a group of the formula (III), $R_4$ is $C_2$-$C_{10}$alkylene, cyclohexylene, cyclohexylenedimethylene, methylenedicyclohexylene, xylylene or $C_4$-$C_{12}$alkylene interrupted by 1 or 2 oxygen atoms or by a group >N—$CH_3$, p and r which can be identical or different are an integer from 2 to 4 and q is zero or 1, $R_2$ is OH, ONa, OK, $C_1$-$C_6$alkoxy, alloyloxy, benzyloxy, $C_1$-$C_6$acyloxy, a group $R_1$-A- or a group of the formula (IV) and n is a number from 1 to 15.

Those compounds of the formula (I) are particularly preferred in which $R_1$ is $C_1$-$C_4$alkyl, $C_1$-$C_4$acyl or ($C_1$-$C_4$alkoxy)-carbonyl, A is a group of the formula (IIa) or (IIb) in which $R_3$ is hydrogen, $C_1$-$C_4$alkyl, cyclohexyl, benzyl or a group of the formula (III), $R_4$ is $C_2$-$C_8$alkylene, cyclohexylenedimethylene, methylenedicyclohexylene or $C_4$-$C_{10}$alkylene interrupted by 1 or 2 oxygen atoms or by a group >N—$CH_3$, p and r which can be identical or different are 2 or 3 and q is zero or 1, and $R_2$ is OH, ONa, OK, $C_1$-$C_4$alkoxy, $C_1$-$C_4$acyloxy, a group $R_1$-A- or a group of the formula (IV) and n is a number from 1 to 10.

Those compounds of the formula (I) are of special interest in which $R_1$ is methyl, acetyl or ($C_1$-$C_2$alkoxy)-carbonyl, A is a group of the formula (IIa) or (IIb) in which $R_3$ is hydrogen, methyl, cyclohexyl or a group of the formula (III), $R_4$ is $C_2$-$C_6$alkylene or $C_4$-$C_{10}$alkylene interrupted by 1 or 2 oxygen atoms, p and r which can be identical or different are 2 or 3 and q is zero or 1, and $R_2$ is OH, ONa, OK, methoxy, acetoxy, a group $R_1$-A- or a group of the formula (IV) and n is a number from 1 to 8.

Those compounds of the formula (I) are of particular interest in which $R_1$ is methyl, acetyl or ($C_1$-$C_2$alkoxy)-carbonyl, A is a group of the formula (IIa) or (IIb) in which $R_3$ is hydrogen, methyl or a group of the formula (III), $R_5$ is hydrogen, methyl or acetyl, $R_4$ is $C_3$-$C_6$alkylene or $C_8$-$C_{10}$alkylene interrupted by 2 oxygen atoms, p and r which can be identical or different are 2 or 3 and q is zero or 1, and $R_2$ is a group $R_1$-A- or a group of the formula (IV) and n is a number from 1 to 5.

Preferred examples of compounds of the formula (I) are those which contain recurring units of the formula (V)

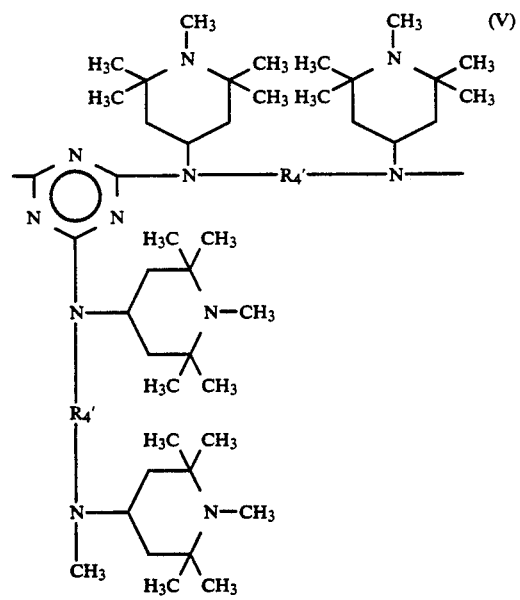

in which $R_3'$ is trimethylene, hexamethylene or 4,7-dioxadecane-1,10-diyl.

The compounds of the formula (I) can be prepared by processes known per se, for example by reacting a compound of the formula (I) where $R_1$=H with a compound of the formula (VI)

$R_1$—X     (VI)

in which $R_1$ is as defined above and X is Cl, Br or I.

If $R_1$ and $R_5$ are methyl, the compounds of the formula (I) are preferably prepared by reacting the corresponding compounds of the formula (I), in which $R_1$ and $R_5$ are hydrogen, with formaldehyde and formic acid, or with formaldehyde and hydrogen in the presence of a hydrogenation catalyst such as palladium or platinum.

If $R_1$ and $R_5$ are acyl, it is possible to use the corresponding acid anhydride as the reagent.

The compounds of the formula (I) with $R_1=H$ can be prepared as described, for example, in U.S. Pat. No. 4,086,204, by reacting cyanuric chloride with a compound of the formula (VIIa) or (VIIb)

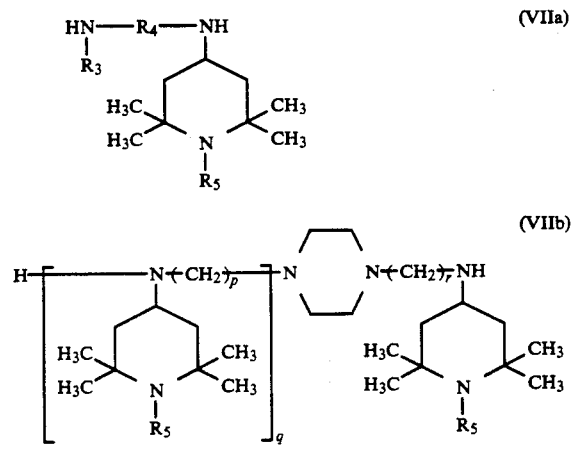

in a cyanuric chloride/compound (VIIa) or (VIIb) molar ratio of 1:2.5 to 1:2, preferably 1:2.4 to 1:2.1, using preferably an aromatic hydrocarbon solvent such as toluene, xylene or trimethylbenzene.

The substitution reactions are preferably carried out by a one-reactor procedure, employing directly the reaction mixture obtained in the preparation of the compounds of the formula (I) with $R_1=H$ at temperatures between e.g. 0° and 150° C., preferably between 10° and 120° C.

The hydrohalic acid set free in the various reactions is preferably neutralized with an inorganic base, for example sodium or potassium hydroxide or carbonate in a quantity at least equivalent to the acid set free.

Depending on the type and molar amounts of the reagents used for the preparation of the instant compounds, the product obtained may be a mixture of the compounds of the formula (I) having different terminal groups $R_2$. This mixture can be separated, if desired, with the aid of for example chromatographic methods, in particular high-pressure liquid chromatography (HPLC).

A preferred embodiment of the instant invention also relates to compounds of the formula (I) obtainable by first reacting cyanuric chloride with a compound of the formula (VIIa) or (VIIb) and subsequently reacting the product obtained with a compound of the formula (VI).

As mentioned at the outset, the compounds of the formula (I) are highly effective in improving the light stability, heat stability and oxidation stability of organic materials, in particular synthetic polymers and copolymers.

Examples of such organic materials which can be stabilized are:

1. Polymers of monoolefins and diolefins, for example polypropylene, polyisobutylene, polybutene-1, polymethylpentene-1, polyisoprene or polybutadiene, as well as polymers of cycloolefins, for instance of cyclopentene or norbornene, polyethylene (which optionally can be crosslinked), for example high-density polyethylene (HDPE), low-density polyethylene (LDPE) and linear low-density polyethylene (LLDPE).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, such as, for example, ethylene/propylene, linear low-density polyethylene (LLDPE) and its mixtures with low-density polyethylene (LDPE), propylene/butene-1, ethylene/hexene, ethylene/ethylpentene, ethylene/heptene, ethylene/octene, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidenenorbornene; as well as mixtures of such copolymers and their mixtures with polymers mentioned in 1) above, for example polypropylene/ethylene-propylene copolymers, LDPE/EVA, LDPE/EAA, LLDPE/EVA and LLDPE/EAA.

3a. Statistical or alternating copolymers of α-olefines with carbon monoxide.

3b. Hydrocarbon resins (for example $C_5$-$C_9$) and hydrogenated modifications thereof (for example tackifiers).

4. Polystyrene, poly-(p-methylstyrene), poly-(α-methylstyrene).

5. Copolymers of styrene or α-methylstyrene with dienes or acrylic derivatives, such as, for example, styrene/acrylonitrile, styrene/alkyl methacrylate, styrene/maleic anhydride, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer and block copolymers of styrene, such as, for example, styrene/butadiene/styrene, styrene/isoprene/styrene, styrene/ethylene/butylene/styrene or styrene/ethylene/propylene/styrene.

6. Graft copolymers of styrene or α-methylstyrene such as, for example, styrene on polybutadiene, styrene on polybutadiene-styrene or polybutadiene-acrylonitrile; styrene and acrylonitrile (or methacrylonitrile) on polybutadiene; styrene and maleic anhydride or maleimide on polybutadiene; styrene, acrylonitrile and maleic anhydride or maleimide on polybutadiene; styrene, acrylonitrile and methyl methacrylate on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under 5), for instance the mixtures known as ABS, MBS, ASA and AES polymers.

7. Halogen-containing polymers, such as polychloroprene, chlorinated rubbers, chlorinated or sulfochlorinated polyethylene, epichlorohydrin homo- and copolymers, polymers from halogen-containing vinyl compounds, as for example polyvinyl chloride, polyvinylidene chloride, polyvinyl fluoride, polyvinylidene fluoride, as well as copolymers thereof, for example vinyl chloride/vinylidene chloride, vinyl chloride/vinyl acetate or vinylidene chloride/vinyl acetate copolymers and ethylene/chlorinated ethylene copolymers.

8. Polymers which are derived from $\alpha,\beta$-unsaturated acids and derivatives thereof, such as polyacrylates and polymethacrylates, polyacrylamide and polyacrylonitrile.

9. Copolymers from the monomers mentioned under 8) with each other or with other unsaturated monomers, such as, for instance, acrylonitrile/butadiene, acrylonitrile/alkyl acrylate, acrylonitrile/alkoxyalkyl acrylate or acrylonitrile/vinyl halide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinyl butyral, polyallyl phthalate or polyallylmelamine; as well as their copolymers with olefins mentioned in 1) above.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and polyoxymethylenes which contain ethylene oxide as a co-monomer; polyacetals modified with thermoplastic polyurethanes, acrylates or MBS.

13. Polyphenylene oxides and sulfides, and mixtures of polyphenylene oxides with polystyrene or polyamides.

14. Polyurethanes which are derived from polyethers, polyesters or polybutadienes with terminal hydroxyl groups on the one hand and on the other hand aliphatic or aromatic polyisocyanates, as well as precursors thereof (polyisocyanates, polyols or prepolymers).

15. Polyamides and copolyamides which are derived from diamines and dicarboxylic acids and/or from aminocarboxylic acids or the corresponding lactams, such as polyamide 4, polyamide 6/6, polyamide 6/10, 6/9, 6/12 and 4/6, polyamide 11, polyamide 12, aromatic polyamides obtained by condensatin of m-xylenediamine and adipic acid; polyamides prepared from hexamethylenediamine and isophthalic and/or terephthalic acid and optionally an elastomer as modifier, for example poly-2,4,4-trimethyl-hexamethyleneterephthalamide or poly-m-phenylene-isophthalamide. Further, copolymers of the aforementioned polyamides with polyolefins, olefin copolymers, ionomers or chemically bonded or grafted elastomers; or with polyethers, such as, for instance, with polyethylene glycols, polypropylene glycols or polytetramethylene glycols. Polyamides or copolyamides modified with EPDM or ABS. Polyamides condensed during processing (RIM-polyamide systems).

16. Polyureas, polyimides and polyamide-imides.

17. Polyesters which are derived from dicarboxylic acids and diols and/or from hydroxycarboxylic acids or the corresponding lactones, such as polyethylene terephthalate, polybutylene terephthalate, poly-1,4-dimethylolcyclohexane terephthalate, poly-[2,2-(4-hydroxyphenyl)-propane] terephthalate and polyhydroxybenzoate as well as block copolyether-esters derived from polyethers having hydroxyl end groups.

18. Polycarbonates and polyester-carbonates.

19. Polysulfones, polyether-sulfones and polyether-ketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low inflammability.

23. Thermosetting acrylic resins, derived from substituted acrylic esters, such as epoxy-acrylates, urethane-acrylates or polyester-acrylates.

24. Alkyd resins, polyester resins or acrylate resins in admixture with melamine resins, urea resins, polyisocyanates or epoxide resins as crosslinking agents.

25. Crosslinked epoxide resins which are derived from polyepoxides, for example from bis-glycidyl ethers or from cycloaliphatic diepoxides.

26. Natural polymers, such as cellulose, rubber, gelatine and derivatives thereof which are chemically modified in a polymer-homologous manner, such as cellulose acetates, cellulose propionates and cellulose butyrates, or cellulose ethers, such as methylcellulose; rosins and their derivatives.

27. Mixtures of polymers as mentioned above, for example PP/EPDM, polyamide 6/EPDM or ABS, PVC/EVA, PVC/ABS, PVC/MBS, PC/ASA, PC/PBT, PVC/CPE, PVC/acrylates, POM/thermoplastic PUR, PC/thermoplastic PUR, POM/acrylate, POM/MBS, PPE/HIPS, PPE/PA 6/6 and copolymers, PA/HDPE, PA/PP, PA/PPE.

28. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, which materials may be used as plasticizers for polymers or as textile spinning oils, as well as aqueous emulsions of such materials.

29. Aqueous emulsions of natural or synthetic rubbers, for example natural latex or latexes of carboxylated styrene/butadiene copolymers.

The compounds of the formula (I) are particularly suitable for improving the light stability, heat stability and oxidation stability of polyolefins, especially polyethylene and polypropylene.

The compounds of the formula (I) can be used in mixtures with organic materials in various proportions depending on the nature of the material to be stabilized, on the end use and on the presence of other additives.

In general, it is appropriate to use, for example, 0.01 to 5% by weight of the compounds of the formula (I), relative to the weight of the material to be stabilized, preferably from 0.05 to 1%.

The compounds of the formula (I) can be incorporated in the polymeric materials by various processes, such as dry mixing in the form of powder, or wet mixing in the form of solutions or suspensions or also in the form of a masterbatch; in such operations, the polymer can be used in the form of powder, granules, solutions, suspensions or in the form of latices.

In general, the compounds of the formula (I) can be added to the polymeric materials before, during or after the polymerization or crosslinking of the said materials.

The compounds of formula (I) can be incorporated into the material to be stabilized in a pure form or encapsulated in waxes, oils or polymers.

The materials stabilized with the products of the formula (I) can be used for the production of mouldings, films, tapes, monofilaments, surface coatings and the like.

If desired, other conventional additives for synthetic polymers, such as antioxidants, UV absorbers, nickel stabilizers, pigments, fillers, plasticizers, antistatic agents, flameproofing agents, lubricants, corrosion inhibitors and metal deactivators, can be added to the mixtures of the compounds of the formula (I) with the organic materials.

Particular examples of additives which can be used in a mixture with the compounds of the formula (I) are:

1. ANTIOXIDANTS 1.1. Alkylated monophenols, for example
2,6-di-tert-butyl-4-methylphenol,
2-tert-butyl-4,6-dimethylphenol, 2,6-di-tert-butyl-4-ethylphenol,
2,6-di-tert-butyl-4-n-butylphenol, 2,6-di-tert-butyl-4-isobutylphenol,
2,6-dicyclopentyl-4-methylphenol, 2-(α-methylcyclohexyl)-4,6-dimethylphenol,
2,6-dioctadecyl-4-methylphenol, 2,4,6-tricyclohexylphenol,
2,6-di-tert-butyl-4-methoxymethylphenol, 2,6-dinonyl-4-methylphenol.

1.2. Alkylated hydroquinones, for example
2,6-di-tert-butyl-4-methoxyphenol,
2,5-di-tert-butylhydroquinone, 2,5-di-tert-amylhydroquinone,
2,6-diphenyl-4-octadecyloxyphenol.

1.3. Hydroxylated thiodiphenyl ethers, for example
2,2'-thiobis(6-tert-butyl-4-methylphenol), 2,2'-thiobis(4-octylphenol),
4,4'-thiobis(6-tert-butyl-3-methylphenol), 4,4'-thiobis(6-tert-butyl-2-methylphenol).

1.4. Alkylidenebisphenols, for example
2,2'-methylenebis(6-tert-butyl-4-methylphenol),
2,2'-methylenebis(6-tert-butyl-4-ethylphenol),
2,2'-methylenebis[4-methyl-6-(α-methylcyclohexyl)-phenol],
2,2'-methylenebis(4-methyl-6-cyclohexylphenol),
2,2'-methylenebis(6-nonyl-4-methylphenol), 2,2'-methylenebis(4,6-di-tert-butylphenol),
2,2'-ethylidenebis(4,6-di-tert-butylphenol),
2,2'-ethylidenebis(6-tert-butyl-4-isobutylphenol),
2,2'-methylenebis[6-(α-methylbenzyl)-4-nonylphenol],
2,2'-methylenebis[6-(α,α-dimethylbenzyl)-4-nonylphenol],
4,4'-methylenebis(2,6-di-tert-butylphenol),
4,4'-methylenebis(6-tert-butyl-2-methylphenol),
1,1-bis(5-tert-butyl-4-hydroxy-2-methylphenyl)butane,
2,6-bis(3-tert-butyl-5-methyl-2-hydroxybenzyl)-4-methylphenol,
1,1,3-tris(5-tert-butyl-4-hydroxy-2-methylphenyl)butane,
1,1-bis(5-tert-butyl-4-hydroxy-2-methylphenyl)-3-n-dodecylmercaptobutane, ethylene glycol bis[3,3-bis(3'-tert-butyl-4'-hydroxyphenyl)butyrate],
bis(3-tert-butyl-4-hydroxy-5-methylphenyl)-dicyclopentadiene,
bis[2-(3'-tert-butyl-2'-hydroxy-5'-methylbenzyl)-6-tert-butyl-4-methylphenyl] terephthalate.

1.5. Benzyl compounds, for example
1,3,5-tris(3,5-di-tert-butyl-4-hydroxybenzyl)-2,4,6-trimethylbenzene, bis(3,5-di-tert-butyl-4-hydroxybenzyl) sulfide, isooctyl 3,5-di-tert-butyl-4-hydroxybenzylmercaptoacetate, bis(4-tert-butyl-3-hydroxy-2,6-dimethylbenzyl) dithiolterephthalate, 1,3,5-tris(3,5-di-tert-butyl-4-hydroxybenzyl) isocyanurate, 1,3,5-tris(4-tert-butyl-3-hydroxy-2,6-dimethylbenzyl) isocyanurate, dioctadecyl 3,5-di-tert-butyl-4-hydroxybenzylphosphonate, calcium salt of monoethyl 3,5-di-tert-butyl-4-hydroxybenzylphosphonate, 1,3,5-tris(3,5-dicyclohexyl-4-hydroxybenzyl) isocyanurate.

1.6. Acylaminophenols, for example lauric acid 4-hydroxyanilide, stearic acid 4-hydroxyanilide, 2,4-bis(octylmercapto)-6-(3,5-di-tert-butyl-4-hydroxyanilino)-s-triazine, octyl N-(3,5-di-tert-butyl-4-hydroxyphenyl)-carbamate.

1.7. Esters of β-(3,5-di-tert-butyl-4-hydroxyphenyl)propionic acid with mono- or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'-bis(hydroxyethyl)oxalic acid diamide.

1.8. Esters of β-(5-tert-butyl-4-hydroxy-3-methylphenyl)propionic acid with mono- or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'bis(hydroxyethyl)oxalic acid diamide.

1.9. Esters of β-(3,5-dicyclohexyl-4-hydroxyphenyl)-propionicacid with mono- or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'-bis(hydroxyethyl)oxalic acid diamide.

1.10. Amides of β-(3,5-di-tert-butyl-4-hydroxyphenyl)-propionic acid e.g.
N,N'-bis(3,5-di-tert-butyl-4-hydroxyphenylpropionyl)hexamethylenediamine,
N,N'-bis(3,5-di-tert-butyl-4-hydroxyphenylpropionyl)trimethylenediamine,
N,N'-bis(3,5-di-tert-butyl-4-hydroxyphenylpropionyl)hydrazine.

2. UV ABSORBERS AND LIGHT STABILIZERS 2.1. 2-(2'-Hydroxyphenyl)benzotriazoles, for example the 5'-methyl, 3',5'-di-tert-butyl, 5'-tert-butyl, 5'-(1,1,3,3-tetramethylbutyl), 5-chloro-3',5'-di-tert-butyl, 5-chloro-3'-tert-butyl-5'-methyl, 3'-sec-butyl-5'-tert-butyl, 4'-octoxy-3',5'-di-tert-amyl and 3',5'-bis-(α,α-dimethylbenzyl) derivatives.

2.2. 2-Hydroxybenzophenones, for example the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, for example 4-tert-butylphenyl salicylate, phenyl salicylate, octylphenyl salicylate, dibenzoylresorcinol, bis(4-tert-butylbenzoyl)resorcinol, benzoylresorcinol, 2,4-di-tert-butylphenyl 3,5-di-tert-butyl-4-hydroxybenzoate and hexadecyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxycinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thiobis[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of 4-hydroxy-3,5-di-tert-butylbenzylphosphonic acid monoalkyl esters, e.g. of the methyl or ethyl ester, nickel complexes of ketoximes, e.g. of 2-hydroxy-4-methylphenyl undecyl ketoxime, nickel complexes of 1-phenyl-4-lauroyl-5-hydroxypyrazole, with or without additional ligands.

2.6. Sterically hindered amines, for example bis(2,2,6,6-tetramethylpiperidyl) sebacate, bis(1,2,2,6,6-pentamethypiperidyl) sebacate, bis(1,2,2,6,6-pentamethylpiperidyl) n-butyl-3,5-di-tert-butyl-4-hydroxybenzylmalonate, the condensation product of 1-hydroxyethyl-2,2,6,6-tetramethyl-4-hydroxypiperidine and succinic acid, the condensation product of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl) 1,2,3,4-butanetetracarboxylate, 1,1'-(1,2-ethanediyl)bis-(3,3,5,5-tetramethylpiperazinone).

2.7. Oxalic acid diamides, for example, 4,4'-dioctyloxyoxanilide, 2,2'-dioctyloxy-5,5'-di-tert-butyloxanilide, 2,2'-didodecyloxy-5,5'-di-tert-butyloxanilide, 2-ethoxy-2'-ethyloxanilide, N,N'-bis(3-dimethylaminopropyl)oxalamide, 2-ethoxy-5-tert-butyl-2'-ethyloxanilide and its mixtures with 2-ethoxy-2'-ethyl-5,4'-di-tert-butyloxanilide and mixtures of ortho- and para-methoxy-disubstituted oxanilides and mixtures of o- and p-ethoxy-disubstituted oxanilides.

2.8 2-(2-Hydroxyphenyl)-1,3,5-triazines, for example
2,4,6-tris(2-hydroxy-4-octyloxyphenyl)-1,3,5-triazine,
2-(2-hydroxy-4-octyloxyphenyl)-4,6-bis(2,4-dimethylphenyl)-1,3,5-triazine,
2-(2,4-dihydroxyphenyl)-4,6-bis(2,4-dimethylphenyl)-1,3,5-triazine,
2,4-bis(2-hydroxy-4-propyloxyphenyl)-6-(2,4-dimethylphenyl)-1,3,5-triazine,
2-(2-hydroxy-4-octyloxyphenyl)-4,6-bis(4-methylphenyl)-1,3,5-triazine,
2-(2-hydroxy-4-dodecyloxyphenyl)-4,6-bis(2,4-dimethylphenyl)-1,3,5-triazine.

3. Metal deactivators, for example N,N'-diphenyloxalic acid diamide, N-salicylal-N'-salicyloylhydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalodihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, tristearyl sorbitol triphosphite, tetrakis(2,4-di-tert-butylphenyl) 4,4'-biphenylenediphosphonite, 3,9-bis(2,4-di-tert-butylphenoxy)-2,4,8,10-tetraoxa-3,9-diphosphaspiro[5.5]undecane.

4. bis. Hydroxylamines, for example dibenzylhydrozylamine, dioctylhydroxylamine, didodecylhydroxylamine, ditetradecylhydroxylamine, dihexadecylhydroxylamine, dioctadecylhydroxylamine, 1-hydroxy-2,2,6,6-tetramethyl-4-piperidyl benzoate, bis(1-hydroxy-2,2,6,6-tetramethyl-4-piperidyl) sebacate.

5. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecy disulfide, pentaerythritol tetrakis(β-dodecylmercapto)propionate.

6. Polyamide stabilizers, for example copper salts in combination with iodides and/or phosphorus compounds and salts of divalent manganese.

7. Basic co-stabilizers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example Ca stearate, Zn stearate, Mg stearate, Na ricinoleate and K palmitate, antimony pyrocatecholate or zinc pyrocatecholate.

8. Nucleating agents, for example 4-tert-butyl-benzoic acid, adipic acid, diphenylacetic acid.

9. Fillers and reinforcing agents, for example calcium carbonate, silicates, glass fibers, asbestos, talc, kaolin, mica, barium sulfate, metal oxides and hydroxides, carbon black, graphite.

10. Other additives, for example plasticizers, lubricants, emulsifiers, pigments, optical brighteners, flameproofing agents, antistatic agents and blowing agents.

The compounds of formula (I) can also be used as stabilizers, especially light stabilizers, for almost all materials known in the art of photographic reproduction and other reproduction techniques as e.g. described in Research Disclosure 1990, 31429 (pages 474 to 480).

The following examples are reported for illustrating the present invention, but without restricting it.

EXAMPLE 1

A solution of 18.4 g (0.1 mol) of cyanuric chloride in 170 ml of xylene is added at ambient temperature to a solution of 82.8 g (0.21 mol) of N,N'-bis(2,2,6,6-tetramethyl-4-piperidyl)-1,6-hexane diamine in 100 ml of xylene.

The addition is carried out slowly, allowing the temperature to rise up to about 45° C. The mixture is stirred for ½ hour at ambient temperature, a solution of 16 g (0.4 mol) of sodium hydroxide in 30 ml of water is added and the mixture is then heated under reflux for 15 hours, with azeotropic removal of the added water and of the water of reaction. After cooling to 90° C. and addition of 200 ml of xylene, the mixture is washed twice with 150 ml of water, while maintaining the temperature at 90° C.

B) A solution containing 55.15 g (0.68 mol) of 37% formaldehyde and 31.3 g (0.68 mol) of formic acid is added in the course of one hour to the above xylene solution heated to 110° C.

After the end of the addition, the mixture is held for 2 hours at 110° C. and, after cooling to ambient temperature, a solution of 28 g (0.7 mol) of sodium hydroxide in 100 ml of water is added, and the mixture is stirred for ½ hour. The organic phase is washed with water, dried over anhydrous Na₂SO₄ and evaporated in vacuo (26 mbar), which gives a compound of melting point 146°–150° C. and $\overline{M}n=2,400$, containing recurring units of the formula

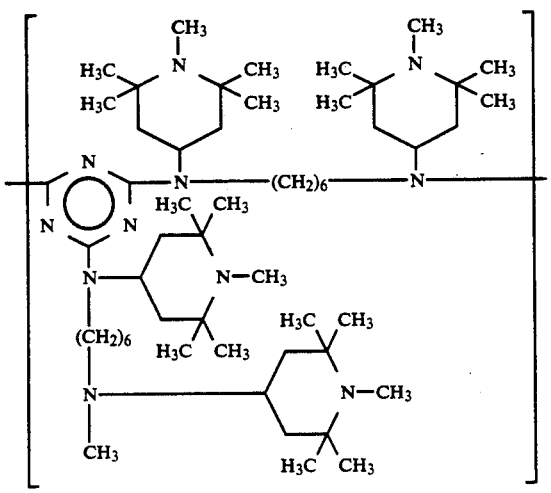

EXAMPLES 2-6

Following the procedure described in Example 1 and using the reagents listed below, the following compounds containing recurring units of the formula

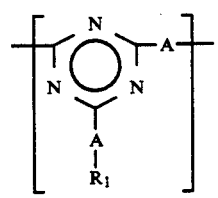

are prepared.
The group

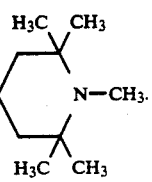 corresponds to 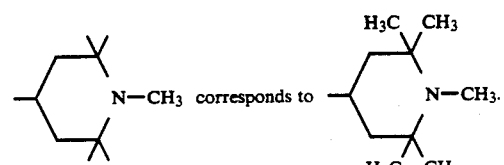

| Example | Reagents | A | $R_1$ | m.p. ($\overline{M}n$) |
|---|---|---|---|---|
| 2 | N,N'-Bis-(2,2,6,6-tetramethyl-4-piperidyl)-1,6-hexanediamine (0.23 mol) Cyanuric chloride (0.10 mol) Formaldehyde (0.70 mol) Formic acid (0.70 mol) | —N—(CH₂)₆—N— (both with tetramethylpiperidyl-N-CH₃ substituents) | —CH₃ | 126–133° C. (1900) |
| 3 | N-(2,2,6,6-Tetramethyl-4-piperidyl)-1,6-hexanediamine (0.23 mol) Cyanuric chloride (0.10 mol) Formaldehyde (0.40 mol) Formic acid (0.40 mol) | —N(H)—(CH₂)₆—N— (with tetramethylpiperidyl-N-CH₃ substituent) | —CH₃ | resin (1400) |
| 4 | N,N'-Bis-(2,2,6,6-tetramethyl-4-piperidyl)-1,3-propanediamine (0.23 mol) Cyanuric chloride (0.10 mol) Formaldehyde (0.70 mol) Formic acid (0.70 mol) | —N—(CH₂)₃—N— (both with tetramethylpiperidyl-N-CH₃ substituents) | —CH₃ | 161–171° C. (1800) |
| 5 | N-(2,2,6,6-Tetramethyl-4-piperidyl)-1-piperazine-ethaneamine (0.225 mol) Cyanuric chloride (0.10 mol) Formaldehyde (0.4 mol) Formic acid (0.4 mol) | —N⌒N—(CH₂)₂—N— (with tetramethylpiperidyl-N-CH₃ substituent) | —CH₃ | 128–136° C. (2300) |

-continued

| Example | Reagents | A | $R_1$ | m.p. ($\overline{M}n$) |
|---|---|---|---|---|
| 6 | N,N'-bis(2,2,6,6-tetramethyl-4-piperidyl)-4,7-dioxadecane-1,10-diamine (0.24 mol) Cyanuric chloride (0.10 mol) Formaldehyde (0.75 mol) Formic acid (0.75 mol) | —N—(CH$_2$)$_3$O(CH$_2$)$_2$O(CH$_2$)$_3$—N— (with 1-methyl-2,2,6,6-tetramethylpiperidyl groups on each N) | —CH$_3$ | 65–74° C. (1800) |

EXAMPLE 7

8.8 g (0.112 mol) of acetyl chloride dissolved in 30 ml of toluene are added slowly at ambient temperature to 41.4 g of the compound prepared according to Example 1A, dissolved in 400 ml of toluene.

After the end of the addition, stirring is continued for 4 hours at ambient temperature, 4.8 g (0.12 mol) of sodium hydroxide dissolved in 30 ml of water are added, the mixture is stirred for 1 hour and the phases are separated. The organic phase is washed with water, dried over anhydrous Na$_2$SO$_4$ and evaporated in vacuo (26 mbar), which gives a compound of melting point 143°–147° C. and $\overline{M}n = 2,350$, containing recurring units of the formula

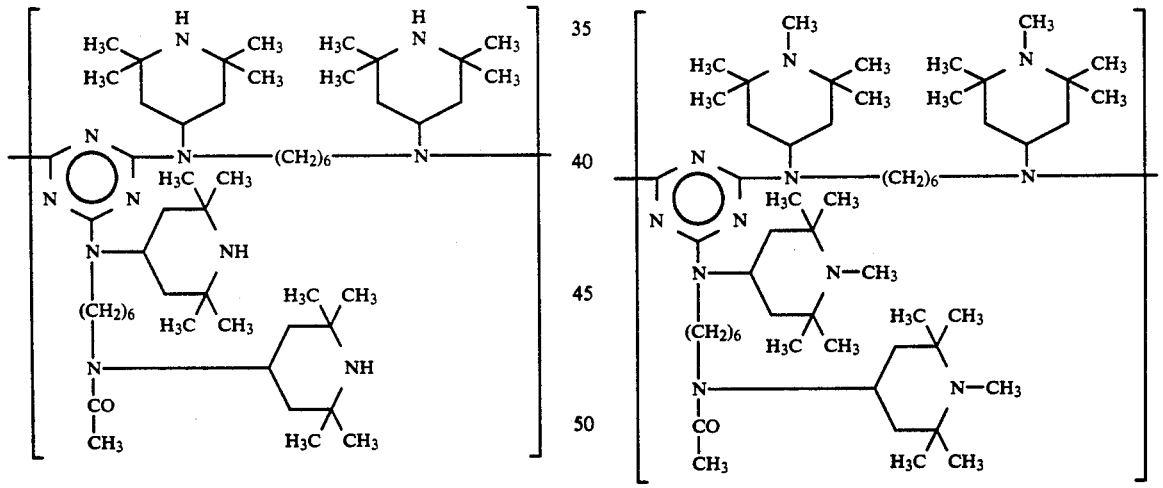

EXAMPLE 8

A solution containing 10.54 g (0.13 mol) of 37% formaldehyde and 5.52 g (0.12 mol) of formic acid is added in the course of ½ an hour to 20 g of the compound prepared according to Example 7, dissolved in 200 ml of toluene and heated to 95°–100° C.

After the end of the addition, the mixture is heated for 2 hours at 100°–105° C. and cooled to ambient temperature, a solution of 6 g (0.15 mol) of sodium hydroxide in 25 ml of water is added and the mixture is stirred for ½ an hour. The organic phase is washed with water, dried over anhydrous Na$_2$SO$_4$ and evaporated in vacuo (26 mbar), which gives a compound of melting point 169°–179° C. and $\overline{M}n = 2500$, containing recurring units of the formula

EXAMPLE 9

20 g of the compound prepared according to Example 1A are suspended in 100 g of acetic anhydride; 0.2 g of 96% H$_2$SO$_4$ is added and the mixture is heated at 110° C. for 6 hours.

The excess acetic anhydride is removed by evaporation in vacuo (1.3 mbar), and the residue is dissolved in 150 ml of dichloromethane.

The solution is washed twice with an aqueous solution of 40 g of sodium hydroxide in 150 ml of water, then washed with water, dried over anhydrous Na$_2$SO$_4$ and evaporated in vacuo (26 mbar), which gives a compound of melting point 248°–257° C. and $\overline{M}n = 2800$, containing recurring units of the formula

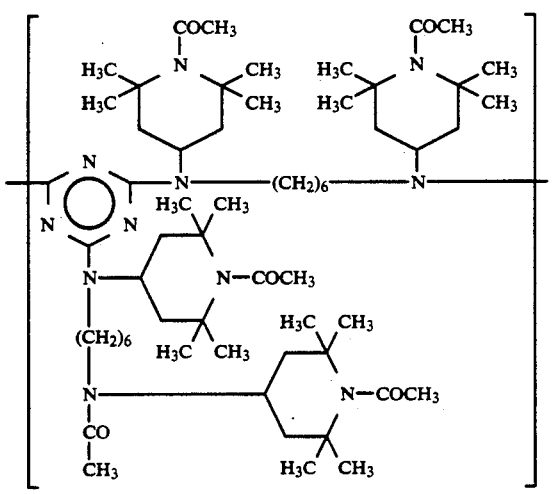

The number average molecular weight indicated in the above examples is determined according to the method described in EP-A-255,990, page 18, line 54 to page 19, line 15.

EXAMPLE 10

Light-stabilizing Action in Polypropylene Fibres 2.5 g of each of the products indicated in Table 1, 1 g of tris-(2,4-di-tert-butylphenyl) phosphite, 0.5 g of calcium monoethyl 3,5-di-tert-butyl-4-hydroxybenzyl-phosphonate, 1 g of calcium stearate and 2.5 g of titanium dioxide are mixed in a slow mixer with 1000 g of polypropylene powder of melt index=12 g/10 minutes (measured at 230° C. and 2.16 kg).

The mixtures are extruded at 200°-230° C. to give polymer granules which are then converted into fibres, using a pilot-type apparatus (Leonard, Sumirago (VA) Italy) and operating under the following conditions:

| Extruder temperature: | 200-230° C. |
| --- | --- |
| Head temperature: | 255-260° C. |
| Stretch ratio: | 1:3.5 |
| Count: | 11 dtex per filament |

The fibres thus prepared are exposed, mounted on white card, in a model 65 WR Weather-O-Meter (ASTM G 26-77) with a black panel temperature of 63° C.

The residual tenacity is measured on samples, taken after various times of exposure to light, by means of a constant-speed tensometer, and the exposure time (in hours) needed to halve the initial tenacity ($T_{50}$) is then calculated. Fibres prepared under the same conditions as indicated above, but without addition of the compounds of the invention, are exposed for comparison.

The results obtained are shown in Table 1:

TABLE 1

| Stabilizer | $T_{50}$ (hours) |
| --- | --- |
| None | 150 |
| Compound from Example 1 | 1810 |
| Compound from Example 4 | 1640 |
| Compound from Example 5 | 1500 |
| Compound from Example 6 | 1820 |
| Compound from Example 7 | 1630 |
| Compound from Example 8 | 1520 |

What is claimed is:

1. A compound of the formula (I)

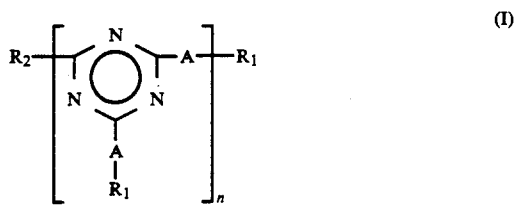

in which $R_1$ is $C_1$-$C_8$alkyl, $C_3$-$C_6$alkenyl, $C_7$-$C_9$phenylalkyl, $C_7$-$C_9$phenylalkyl mono-, di-or tri-substituted on the phenyl by $C_1$-$C_4$alkyl, $C_1$-$C_8$acyl or ($C_1$-$C_8$alkoxy)-carbonyl, A is a group of the formula (IIa) or (IIb)

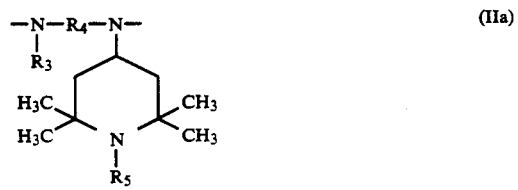

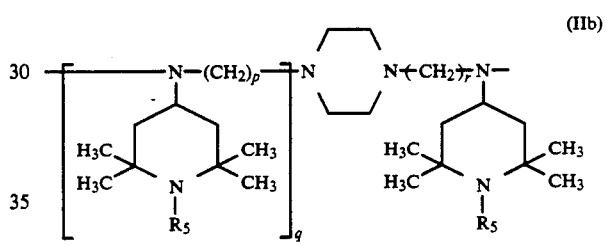

in which $R_3$ is hydrogen, $C_1$-$C_8$alkyl, $C_5$-$C_8$cycloalkyl which is unsubstituted or mono-, di- or tri-substituted by $C_1$-$C_4$alkyl, $C_7$-$C_9$phenylalkyl, $C_7$-$C_9$phenylalkyl mono-, di- or tri-substituted on the phenyl by $C_1$-$C_4$alkyl, or a group of the formula (III),

$R_5$ is hydrogen, $C_1$-$C_8$alkyl, O, OH, NO, $CH_2CN$, $C_1$-$C_{12}$alkoxy, $C_5$-$C_{12}$cycloalkoxy, $C_3$-$C_6$alkenyl, $C_7$-$C_9$phenylalkyl, $C_7$-$C_9$phenylalkyl mono-, di- or tri-substituted on the phenyl by $C_1$-$C_4$alkyl, or $C_1$-$C_8$acyl and $R_4$ is $C_2$-$C_{12}$alkylene, cyclohexylene, cyclohexylenedimethylene, methylenedicyclohexylene, xylylene or $C_4$-$C_{12}$alkylene interrupted by 1, 2 or 3 oxygen atoms or by a group >N—$CH_3$, p and r which can be identical or different are integers from 2 to 6 and q is zero or 1, and $R_2$ is OH, ONa, OK, $C_1$-$C_8$alkoxy, $C_3$-$C_6$alkenyloxy, $C_7$-$C_9$phenylalkoxy, $C_1$-$C_8$acyloxy or a group $R_1$-A-, with $R_1$ and A being as defined above, or $R_2$ can also be a group of the formula (IV)

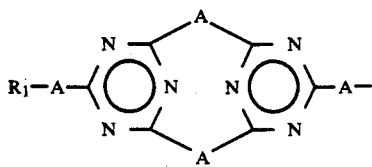

in which $R_1$ and A are as defined above and when $R_2$ is a group of the formula (IV), the terminal group $R_1$ which is outside of the brackets in the formula (I) is additionally a group

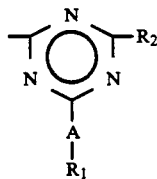

in which $R_1$ and A are as defined above and n is a number from 1 to 20.

2. A compound of the formula (I) according to claim 1, in which $R_5$ is hydrogen, $C_1$-$C_4$alkyl, OH, $C_6$-$C_8$alkoxy, $C_5$-$C_8$cycloalkoxy, allyl, benzyl or acetyl.

3. A compound of the formula (I) according to claim 1, in which $R_1$ is $C_1$-$C_6$alkyl, allyl, benzyl, $C_1$-$C_6$acyl or ($C_1$-$C_6$alkoxy)-carbonyl, A is a group of the formula (IIa) or (IIb) in which $R_3$ is hydrogen, $C_1$-$C_6$alkyl, cyclohexyl which is unsubstituted or mono-, di- or tri-substituted by $C_1$-$C_4$alkyl, benzyl or a group of the formula (III), $R_4$ is $C_2$-$C_{10}$alkylene, cyclohexylene, cyclohexylenedimethylene, methylenedicyclohexylene, xylylene or $C_4$-$C_{12}$alkylene interrupted by 1 or 2 oxygen atoms or by a group >N—CH$_3$, p and r which can be identical or different are an integer from 2 to 4 and q is zero or 1, $R_2$ is OH, ONa, OK, $C_1$-$C_6$alkoxy, allyloxy, benzyloxy, $C_1$-$C_6$acyloxy, a group $R_1$-A- or a group of the formula (IV) and n is a number from 1 to 15.

4. A compound of the formula (I) according to claim 1, in which $R_1$ is $C_1$-$C_4$alkyl, $C_1$-$C_4$acyl or ($C_1$-$C_4$alkoxy)-carbonyl, A is a group of the formula (IIa) or (IIb) in which $R_3$ is hydrogen, $C_1$-$C_4$alkyl, cyclohexyl, benzyl or a group of the formula (III), $R_4$ is $C_2$-$C_8$alkylene, cyclohexylenedimethylene, methylenedicyclohexylene or $C_4$-$C_{10}$alkylene interrupted by 1 or 2 oxygen atoms or by a group >N—CH$_3$, p and r which can be identical or different are 2 or 3 and q is zero or 1, and $R_2$ is OH, ONa, OK, $C_1$-$C_4$alkoxy, $C_1$-$C_4$acyloxy, a group $R_1$-A- or a group of the formula (IV) and n is a number from 1 to 10.

5. A compound of the formula (I) according to claim 1, in which $R_1$ is methyl, acetyl or ($C_1$-$C_2$alkoxy)-carbonyl, A is a group of the formula (IIa) or (IIb) in which $R_3$ is hydrogen, methyl, cyclohexyl or a group of the formula (III), $R_4$ is $C_2$-$C_6$alkylene or $C_4$-$C_{10}$alkylene interrupted by 1 or 2 oxygen atoms, p and r which can be identical or different are 2 or 3 and q is zero or 1, and $R_2$ is OH, ONa, OK, methoxy, acetoxy, a group $R_1$-A- or a group of the formula (IV) and n is a number from 1 to 8.

6. A compound of the formula (I) according to claim 1, in which $R_1$ is methyl, acetyl or ($C_1$-$C_2$alkoxy)-carbonyl, A is a group of the formula (IIa) or (IIb) in which $R_3$ is hydrogen, methyl or a group of the formula (III), $R_5$ is hydrogen, methyl or acetyl, $R_4$ is $C_3$-$C_6$alkylene or $C_8$-$C_{10}$alkylene interrupted by 2 oxygen atoms, p and r which can be identical or different are 2 or 3 and q is zero or 1, and $R_2$ is a group $R_1$-A- or a group of the formula (IV) and n is a number from 1 to 5.

7. A compound of the formula (I) according to claim 1, which contains recurring units of the formula (V)

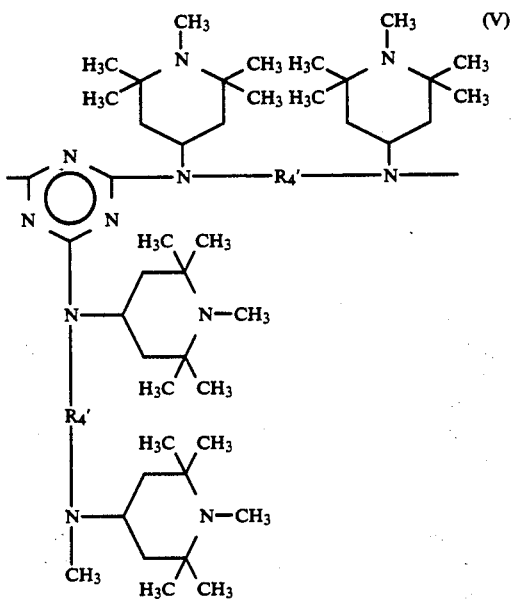

in which $R_4'$ is trimethylene, hexamethylene or 4,7-dioxadecane-1,10-diyl.

* * * * *